United States Patent
Chu

(10) Patent No.: US 8,795,152 B2
(45) Date of Patent: Aug. 5, 2014

(54) DEVICES AND METHODS FOR DELIVERING SUTURES AND IMPLANTS

(75) Inventor: Michael S. H. Chu, Brookline, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 241 days.

(21) Appl. No.: 13/215,621

(22) Filed: Aug. 23, 2011

(65) Prior Publication Data

US 2012/0065461 A1 Mar. 15, 2012

Related U.S. Application Data

(60) Provisional application No. 61/382,226, filed on Sep. 13, 2010.

(51) Int. Cl.
*A61F 2/00* (2006.01)
*A61B 17/04* (2006.01)

(52) U.S. Cl.
USPC .................................. 600/37; 606/145

(58) Field of Classification Search
USPC .................. 600/37; 606/139, 144–150
See application file for complete search history.

(56) References Cited

U.S. PATENT DOCUMENTS

| | | | | |
|---|---|---|---|---|
| 5,540,704 | A | * | 7/1996 | Gordon et al. ............... 606/144 |
| 5,860,992 | A | * | 1/1999 | Daniel et al. ................ 606/145 |
| 6,152,934 | A | | 11/2000 | Harper et al. |
| 6,443,963 | B1 | | 9/2002 | Baldwin et al. |
| 2002/0188301 | A1 | * | 12/2002 | Dallara et al. ............... 606/104 |
| 2007/0270885 | A1 | | 11/2007 | Weinert et al. |
| 2009/0281377 | A1 | | 11/2009 | Newell et al. |

OTHER PUBLICATIONS

Capio CL Transvaginal Suture Fixation to Cooper's Ligament for Sling Procedures, Boston Scientific, 4 pages, 2009.
Capio Suture Capuring Device, Boston Scientific, 4 pages, 2009.
Pinnacle Pelvic Floor Repair Kit Devices, Boston Scientific, 4 pages, 2009.
Uphold Vaginal Support System, Boston Scientific, 4 pages, 2009.

* cited by examiner

*Primary Examiner* — John Lacyk

(57) ABSTRACT

A medical device for the delivery of sutures and implants through tissue of a patient's body. The medical device includes a handle, an elongated shaft member, a needle carrier, and a slideable mechanism. A method of delivering a suture or an implant includes inserting and deploying a medical device including a handle, an elongated shaft member, a needle carrier, and a slideable mechanism into tissue of a patient's body.

17 Claims, 11 Drawing Sheets

DEVICES AND METHODS FOR DELIVERING SUTURES AND IMPLANTS

CROSS-REFERENCE TO RELATED CASE

This claims priority to and the benefit of Provisional U.S. Patent Application Ser. No. 61/382,226 filed on Sep. 13, 2010, the entirety of which is incorporated herein by reference.

TECHNICAL FIELD

The invention relates to devices and methods for delivering sutures and/or implants, and more particularly, to minimally invasive devices and methods for delivering sutures or implants through tissue of a patient's body.

BACKGROUND INFORMATION

The delivery of a suture and/or implant, such as a pelvic floor repair (PFR) implant, into the pelvic or other regions of the human body can be an invasive surgical procedure.

Some commercially available medical devices are limited by the manner in which they access the pelvic or other regions of the human body. For example, such devices are generally too cumbersome in size and length to be ergonomic or minimally invasive. In addition, these devices generally require numerous components which require tight tolerance and expensive parts for assembly. Accordingly, these devices do not provide the functionality and maneuverability necessary to perform surgical procedures involving the delivery of sutures and/or implants in a less invasive manner.

SUMMARY OF THE INVENTION

The invention relates to minimally invasive devices and methods for delivering sutures or implants through tissue of a patient's body. A medical device according to the invention is less invasive and more manipulatable relative to existing devices in the delivery and placement of sutures and implants within a region of a human body. This is accomplished, for example, by devices according to the invention having minimal components and a reduced profile compared to existing devices. A medical device according to the invention allows an operator to make a minimum dissection profile within a region of a patient's body such that the medical device may be inserted into the region to deliver a suture or implant in a less invasive manner while retaining robust functionality. In contrast to existing commercial devices which require large dissection profiles to deliver sutures or implants, such as PFR implants, the dissection profile required by devices according to the invention are significantly smaller, such as equal or about equal to the diameter of an operator's finger, the profile of the medical device, or the profile of the PFR implant.

In one aspect, the invention relates to a medical device that includes a handle, an elongated shaft member, a needle carrier, and a slideable mechanism. The elongated shaft member extends from the handle and the needle carrier extends from a distal end of the elongated shaft member. The needle carrier has a channel that is configured to receive a needle that can be coupled to a suture or a portion of a pelvic floor repair implant. The slideable mechanism includes a knob member and an outer shaft. The outer shaft extends from the knob member and the outer shaft includes a needle catch. The knob member and the outer shaft are disposed coaxially over the elongated shaft member and are manipulatable by an operator of the device to slide along at least a portion of the length of the elongated shaft member. The needle catch is configured to receive and retain the needle carried by the needle carrier.

In one embodiment according to this aspect of the invention, the slideable mechanism can be configured to move the needle catch relative to the needle carrier when the knob member is manipulated by the operator of the device.

In another embodiment according to this aspect of the invention, the slideable mechanism can be configured to move the needle carrier relative to the needle catch when the knob member is manipulated by the operator of the device.

The needle catch of the medical device can be configured to receive the needle through at least one opening and to retain the needle after the needle carrier is retracted. The needle carrier can include a substantially C-shaped configuration. The needle catch can also be comprised of elastomeric materials. The needle catch can also be integrally formed with the outer shaft. The needle can also include a sharpened tip for penetrating the tissue of the patient's body.

The distal portion of the elongated shaft member of the medical device can be deflectable off of the longitudinal axis by manipulation by the operator of the device. The proximal portion of the elongated shaft member can also include at least one detent. The detent can be configured to prevent movement of the knob member beyond the detent.

In a second aspect, the invention relates to a medical device that includes a handle, an elongated shaft member, a needle carrier, and a slideable mechanism. The elongated shaft member extends from the handle and the needle carrier extends from a distal end of the elongated shaft member. The needle carrier has a channel that is configured to receive a needle that can be coupled to a suture or a portion of a pelvic floor repair implant. The slideable mechanism includes a knob member and an outer shaft. The outer shaft extends from the knob member and the outer shaft includes a needle catch. The elongated shaft member extends off at an angle from the outer shaft. The knob member and the outer shaft are manipulatable by an operator of the device to slide along at least a portion of the length of the elongated shaft member. The needle catch is configured to receive and retain the needle carried by the needle carrier.

In one embodiment according to this aspect of the invention, the slideable mechanism can be configured to move the needle carrier relative to the needle catch when the knob member is manipulated by the operator of the device.

The needle catch of the medical device can be configured to receive the needle through at least one opening and to retain the needle after the needle carrier is retracted. The needle catch can also be comprised of elastomeric materials. The needle catch can also be integrally formed with the outer shaft. The distance between the needle catch and the needle carrier can define an opening for receiving tissue of a patient's body.

The distal portion of the elongated shaft member of the medical device can be deflectable off of the longitudinal axis by manipulation by the operator of the device. The proximal portion of the elongated shaft member can also include at least one detent. The detent can be configured to prevent movement of the knob member beyond the detent.

In a third aspect, the invention relates to a method of delivering a suture or an implant. The method includes provide a medical device, such as one of the medical devices described above, inserting a needle coupled to a suture or a portion of a pelvic floor repair implant into the needle carrier of the medical device, dissecting a patient's body to create an opening within the patient's body, inserting the elongated shaft member and the needle carrier of the medical device through the opening, manipulating the needle carrier around a tissue portion within the opening, and manipulating the slideable mechanism of the medical device to move the needle catch relative to the needle carrier to cause the needle to be pushed through the tissue portion into the needle catch of the medical device.

These and other objects, along with advantages and features of the invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same or similar parts throughout the different views. Also, the drawings are not necessarily to scale, emphasis instead generally being placed upon illustrating the principles of the invention.

DESCRIPTION

In general, the invention relates to medical devices, including suturing devices and devices for use in the delivery of implants, which are less invasive and more manipulative for the delivery of sutures and the placement of pelvic floor repair (PFR) and/or other implants.

Figure 1A:
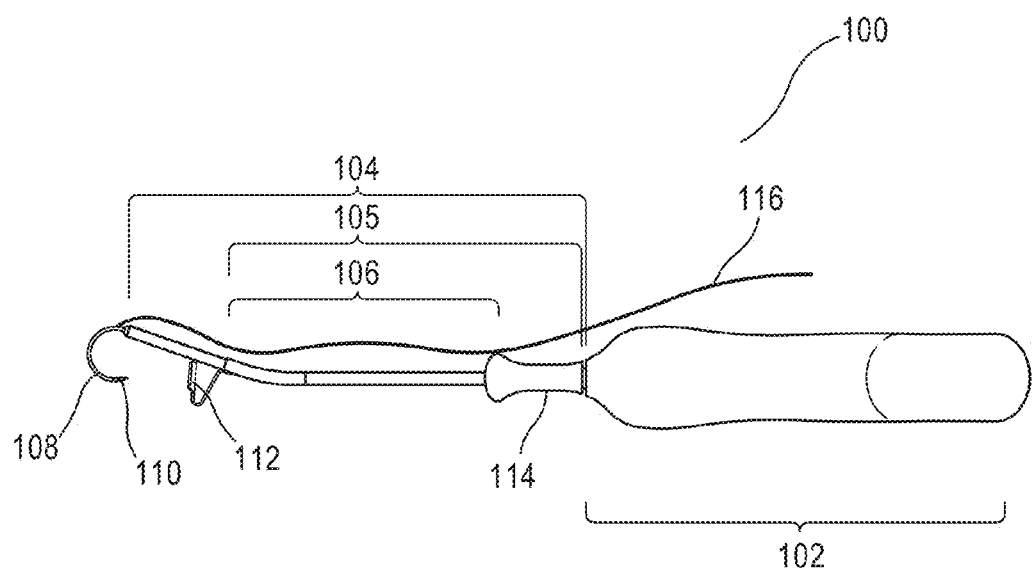
FIG. 1A is a plan view of an embodiment of a medical device for use in delivering a suture and/or an implant.
Figure 1B:
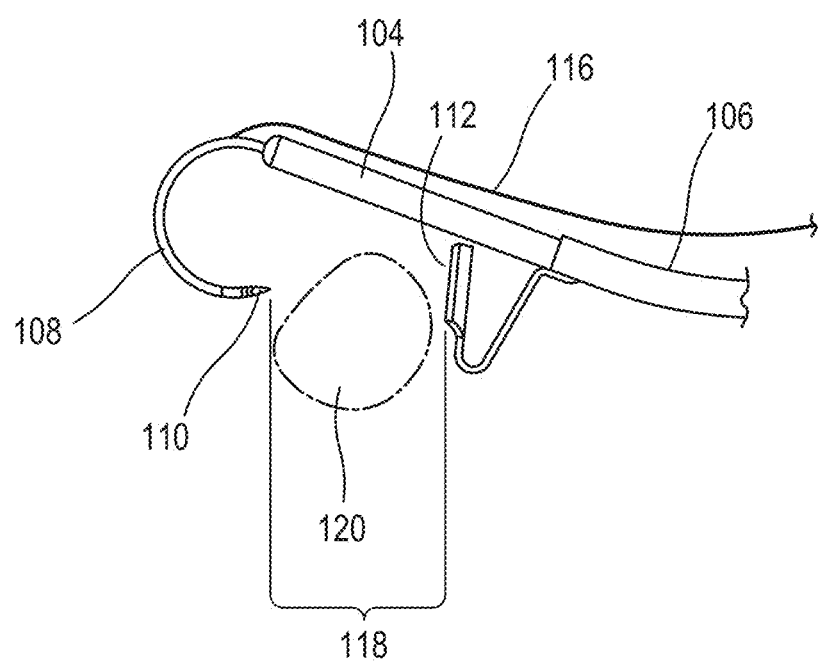
FIG. 1B is an exploded plan view of a distal portion of the medical device.

Referring to FIGS. 1A and 1B, in one embodiment according to the invention, a medical device 100 includes a handle 102, an elongated shaft member 104, a slideable mechanism 105, an outer shaft 106, a needle carrier 108, a needle 110, a needle catch 112, a knob member 114, and a suture 116.

The handle 102 is configured to allow an operator (such as a physician or other medical personnel) to grasp and hold the handle 102 during a surgical procedure. The handle 102 may be provided in various shapes and sizes in order to accommodate the requirements of the operator. The handle 102 may be constructed from various materials, such as thermoplastic elastomers.

A proximal portion of the elongated shaft member 104 extends into and is partially disposed within the handle 102. A distal portion of elongated shaft member 104 is capable of being deflected off of the longitudinal axis of the elongated shaft member 104 into a shape and retaining the shape during use. The elongated shaft member 104 may be provided in various configurations, such as a solid circular rod. Other configurations include, but are not limited to, an oval, rectangular, square, triangular, or keyed shaped rod. Such configurations can prevent rotation of the elongated shaft member 104 as well as allow the elongated shaft member 104 to maintain a consistent alignment. The elongated shaft member 104 may be constructed from various materials including, but not limited to, metals and metal alloys. The elongated shaft member 104 may also be constructed from flexible materials to facilitate bendability. The elongated shaft member 104 can be molded as a single piece into the handle 102. The elongated shaft member 104 and the needle carrier 108 may also be constructed to be a single operative component.

The needle carrier 108 extends out of a distal end of the elongated shaft member 104. The needle carrier 108 includes a channel that is configured to receive the needle 110. The needle carrier 108 further includes a substantially C-shaped configuration.

The needle 110 can be coupled to the suture 116. The needle 110 can also be coupled to a portion of an implant, such as a PFR implant. The distance between the needle 110 and the needle catch 112 defines an opening 118 to receive tissue 120 of a patient's body.

The slideable mechanism 105 includes the outer shaft 106 and the knob member 114. The outer shaft 106 extends from the knob member 114. The outer shaft 106 and the knob member 114 are disposed coaxially over the elongated shaft member 104. The slideable mechanism 105 also comprises the needle catch 112. The needle catch 112 can be integrally formed with the outer shaft 106. The needle catch 112 is configured to receive and retain the needle 110 carried by the needle carrier 108. The slideable mechanism 105 is configured to move the needle catch 112 relative to the needle carrier 108 when the knob member 114 is manipulated by the operator of the device. The knob member 114 is configured to receive at least one finger of an operator of the device such that the knob member 114 and is manipulatable and can slide the knob member 114 and the outer shaft 106 along at least a portion of the length of the elongated shaft member 104. The outer shaft 106 and elongated shaft member 104 may also be constructed to be snap-fitted or riveted together rather than being coaxially located.

Figure 1C:
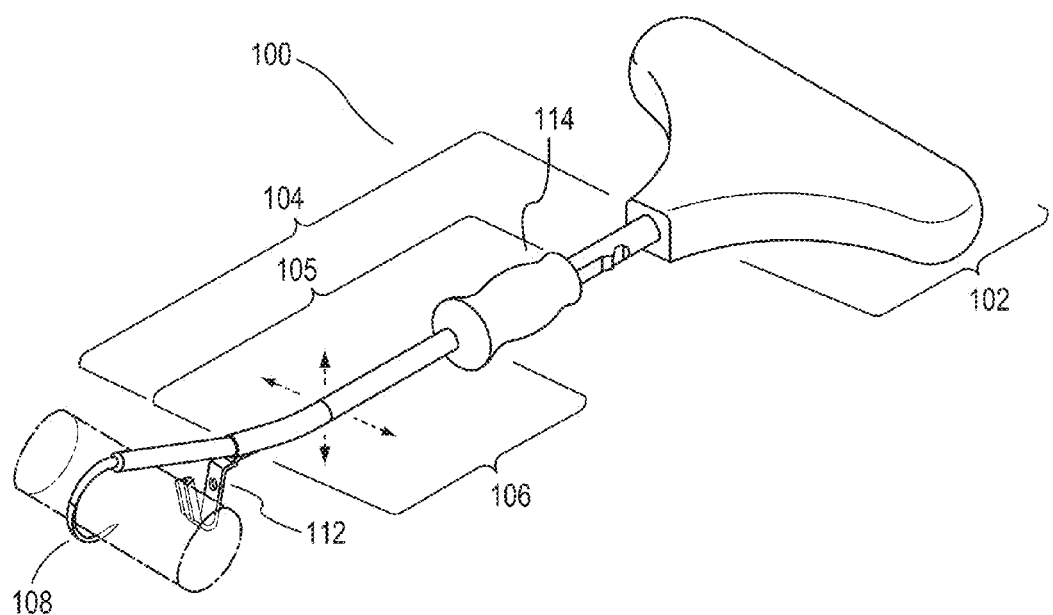
FIG. 1C is a perspective view of the medical device similar to FIG. 1A but including a substantially T-shaped handle.

Referring to FIG. 1C, the medical device 100 may be configured to include a substantially T-shaped handle 102. As with the first embodiment described with respect to FIGS. 1A-1B, the slideable mechanism 105 is disposed over the elongated shaft member 104, but in this second embodiment, the slideable mechanism 105 is configured to move the needle carrier 108 relative to the needle catch 112 when the knob member 114 is manipulated by the operator of the device. In operation, the operator can manipulate the slideable mechanism 105 by sliding the knob member 114 and the outer shaft 106 towards the needle catch 112. This process allows the operator to advance the needle carrier 108 until the needle 110 pierces through tissue and enters the needle catch 112.

Figure 1D:
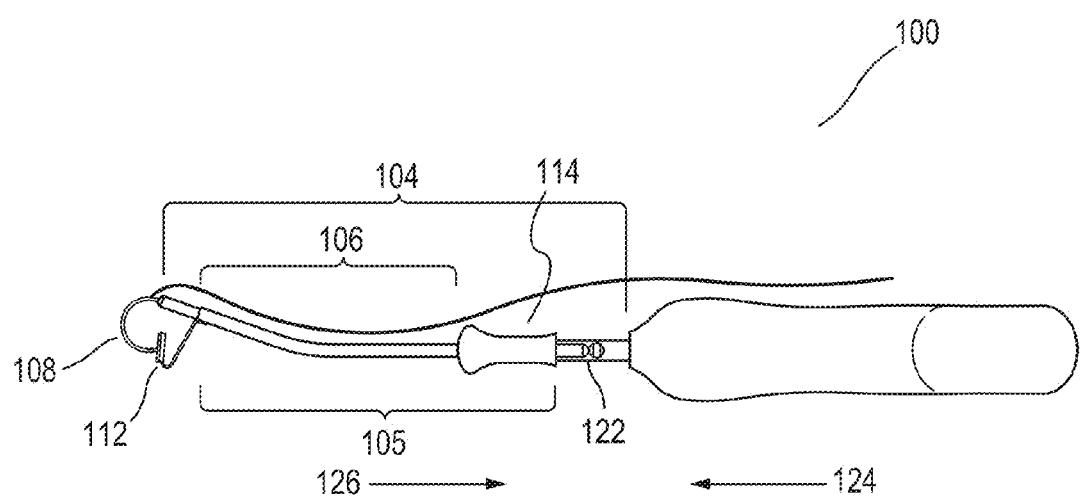
FIG. 1D is a plan view of the needle carrier engaged with the needle catch.
Figure 1E:
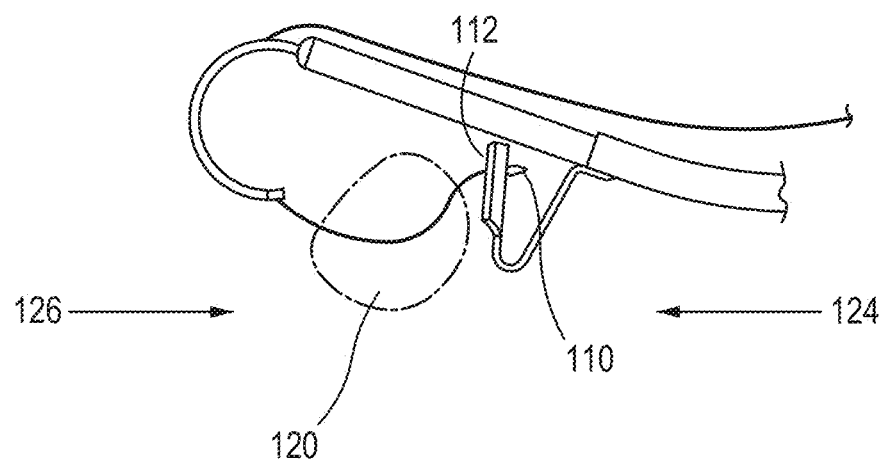
FIG. 1E is a plan view of the needle catch being retracted from the needle catch.
Figure 2A:
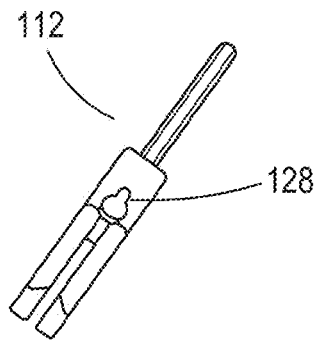
FIG. 2A is a top plan view of the needle catch.
Figure 2B:
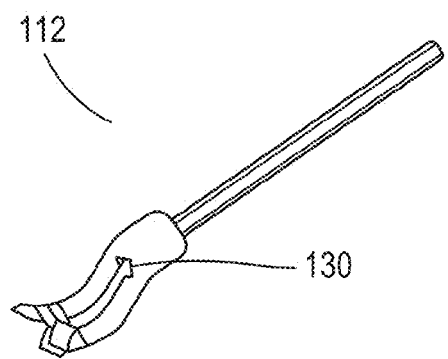
FIG. 2B is a perspective view of the needle catch.
Figure 2C:
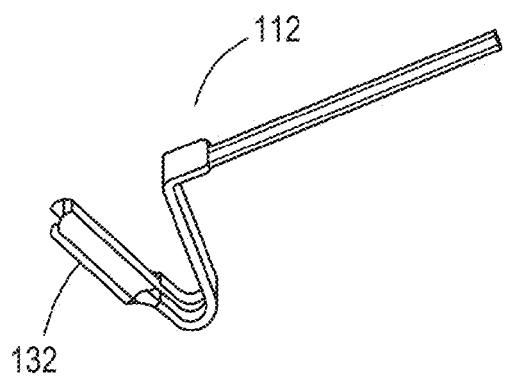
FIG. 2C is a perspective view of the needle catch.
Figure 3A:
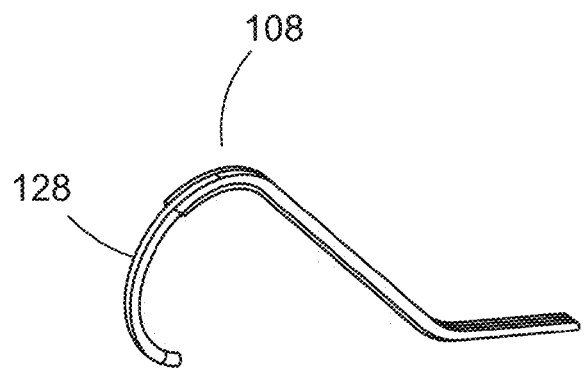
FIG. 3A is a perspective view of the needle carrier.
Figure 3B:
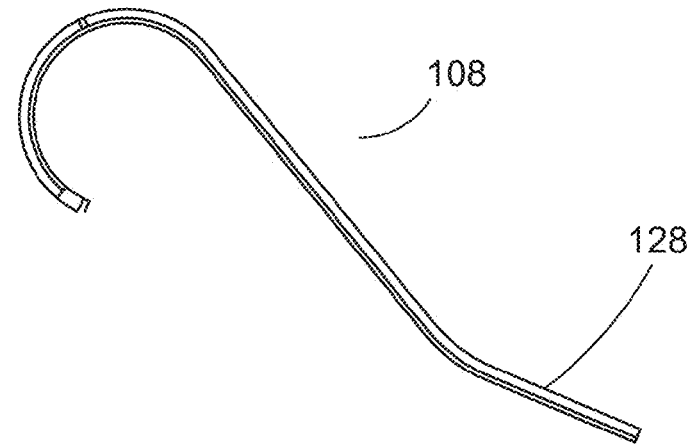
FIG. 3B is a plan view of the needle carrier.
Figure 3C:
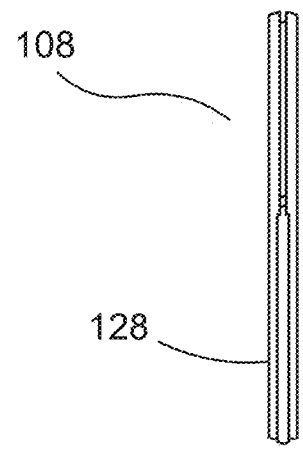
FIG. 3C is a top plan view of the needle carrier.

Referring to FIGS. 1D and 1E, an operator of the medical device 100 can manipulate the slideable mechanism 105 coaxially over the elongated shaft member 104 such that the needle catch 112 moves relative to the stationary needle carrier 108. In operation, the operator can manipulate the slideable mechanism 105 by sliding the knob member 114 and the outer shaft 106 in a first direction 124 towards the needle carrier 108. This process allows the operator to advance the needle catch 112 until the needle 110 (FIG. 1A) pierces through the tissue 120 (FIG. 1B) and enters the needle catch 112.

Once the needle 110 penetrates through the tissue 120 and is retained in the needle catch 112, the operator can retract the slideable mechanism 105 in a second direction 126 by sliding the knob member 114 and the outer shaft 106 towards the handle 102. The needle 110 is retained in the needle catch 112 as the needle catch 112 is retracted relative to the stationary needle carrier 108. The elongated shaft member 104 includes at least one detent 122 to prevent the operator from moving the slideable mechanism 105 beyond the at least one detent 122.

The needle 110 may include a sharp, tapered point to facilitate the penetration of the tissue 120 and manipulate entry into the needle catch 112. The needle 110 may also include a circular back edge to facilitate the placement of the needle 110 within the needle catch 112. The needle 110 is held within the needle carrier 108 by a frictional fit. The needle 110 may be configured for use with various configurations of the needle catch 112. The needle 110 may be dart-shaped, ring-shaped, or cone-shaped.

Referring to FIGS. 1A-1E, 2A, 2B, and 2C, the needle catch 112 receives the needle 110 through a first opening 128. The first opening 128 is configured to deflect slightly to allow the needle 110 to pass through the first opening 128. Once the needle 110 has passed through the first opening 128, the needle catch 112 is pulled in the second direction 126 away from the needle carrier 108, thereby releasing the needle 110 from the needle carrier 108. The first opening 128 is chosen to be smaller in dimension than the needle 110. This causes the needle catch 112 to retain the needle 110, because, due to the circular rear surface of the needle 110, the needle 110 cannot pass back through the opening 128 when the needle catch 112 is retracted in the second direction 126.

Once the medical device 100 is external to the patient's body, the needle 110 may be removed from the needle catch 112 by sliding the needle 110 through a second opening 130. The second opening 130 is sized to allow the needle 110 to pass through without resistance. In one embodiment, the needle catch 112 includes a plurality of openings 128 and enlarged portions 130.

The needle catch 112 can include at least one angled portion 132 to prevent misalignment and/or deflection of the needle catch 112 during the placement of a suture and/or implant. The needle catch 112 may be constructed from materials including, but not limited, metals, plastic, elastomeric, and fabric. The needle catch 112 may be fabricated by means of stamping, laser machining, or chemical etching and may be constructed to be any size or shape.

Referring to FIGS. 1A-1E, 3A, 3B, and 3C, the needle carrier 108 includes a channel 134 to facilitate the passage of the suture 116 and/or a portion of an implant. The needle carrier 108 may be constructed of various sizes, shapes, and lengths. For example, the needle carrier 108 can have a substantially S-shaped configuration. The needle carrier 108 can also have a tapered diameter, a longer or shorter length, and different angle of bends along its outer surface.

Referring to FIGS. 1A-3C, an operator may hold the handle 102 of the medical device 100 of FIG. 1A with one hand, such as between a forefinger and thumb, and may manipulate the knob member 114 with a finger of the second hand. However, in other embodiments, the medical device 100 can be used by one hand only. The operator may use either hand or both hands to operate the medical device 100. The elongated shaft member 104 includes an outer surface that is exposed such that the operator can touch the outer surface and manipulate the needle carrier 108 to introduce tissue or a ligament between the needle carrier 108 and the needle catch 112. The operator's forefinger of one hand can be used to guide the outer surface of the elongated shaft member 104, while the other hand of the operator can be used to hold the handle 102. The handle 102 may be configured such that it is longer or shorter in length.

In one embodiment, the medical device 100 of FIG. 1A can be inserted into a patient's pelvic region to perform a PFR implant procedure. A patient's pelvic region typically includes a sacrospinous ligament (SSL) and an arcus tendineae fascia pelvis (ATFP). Once the opening 118 is placed onto the SSL, the operator may place his/her finger directly on top of the needle carrier 108 to position the needle carrier 108 prior to manipulating the slideable mechanism 105.

The medical device 100 may be used as part of palpation by an operator prior to delivering a PFR implant. The ATFP may be the first landmark that the operator feels for after dissection of the pelvic region. Dissection of the pelvic region may be required to access the SSL for placing the PFR implant. The dissection profile required as part of palpation by an operator may be equal to the diameter of the operator's finger, the profile of the medical device 100, or the profile of the PFR implant. The profile of the medical device 100 may minimize the dissection profile within the patient's pelvic region. A smaller dissection profile typically provides the patient with an expedited healing process. Upon locating the ATFP, the operator may move his/her finger onto the SSL. The operator may then insert the elongated shaft member 104 into the patient's pelvic region and slide the elongated shaft member 104 along his/her finger towards the SSL, so that the needle carrier 108 may deliver an implant to the SSL. The operator could then manipulate the slideable mechanism 105 in the first direction 124, thereby causing the needle catch 112 to move towards the needle carrier 108 and push the needle 110 through the SSL. As the needle 110 is pushed through the SSL, the needle 110 pulls the implant through the SSL. As the operator continues to manipulate the slideable mechanism 105 in the first direction 124, the needle catch 112 continues to advance towards the needle carrier 108 and the needle 110. The operator continues to manipulate the slideable mechanism 105 until the needle 110 contacts and becomes captured by the needle catch 112. An audible or a click can be heard and/or felt by the operator as the needle catch 112 snaps closed behind the needle 110. In other embodiments, the slideable mechanism 105 is advanced to a mark indicated on the elongated shaft member 104 (not shown in Figures).

Figure 4A:
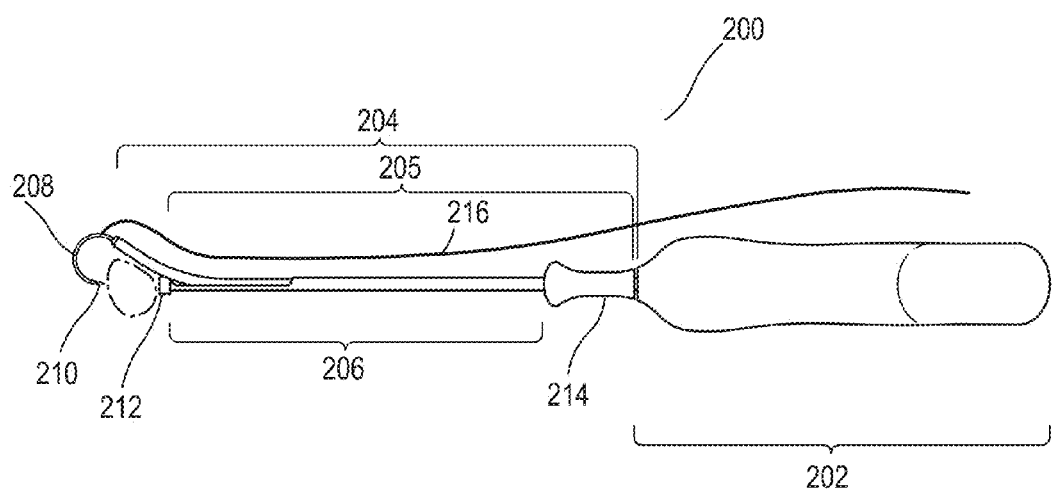
FIG. 4A is a perspective view of another embodiment of the medical device of FIG. 1A.
Figure 4B:
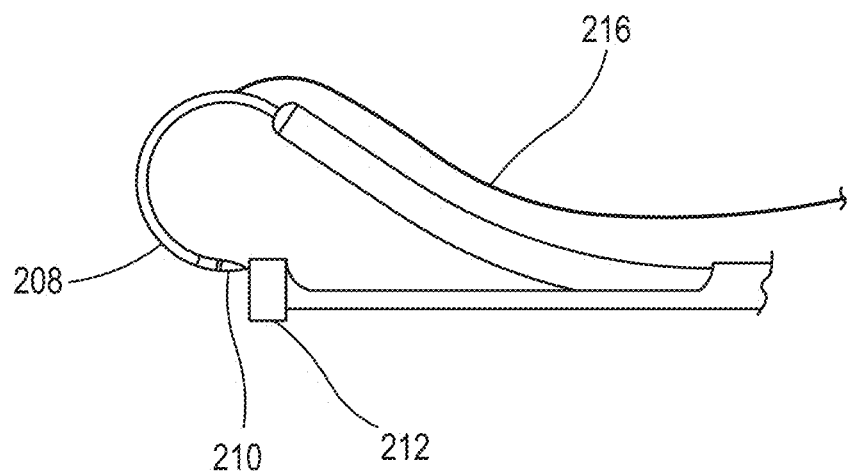
FIG. 4B is an exploded plan view of a distal portion of the medical device of FIG. 4A.

Referring to FIGS. 4A and 4B, another embodiment of the invention is depicted as a medical device 200. The medical device 200 includes a handle 202, an elongated shaft member 204, a slideable mechanism 205, an outer shaft 206, a needle carrier 208, a needle 210, a needle catch 212, a knob member 214, and a suture 216. As with the first embodiment described with respect to FIGS. 1A-3C, the slideable mechanism 205 is disposed over the elongated shaft member 204, but in this second embodiment, the slideable mechanism 205 does not move coaxially over the elongated shaft member 204. The elongated shaft member 204 extends off at an angle, such as 45° degrees, from the outer shaft 206. In operation, the medical device 200 functions as does the medical device 100 of FIGS. 1A-3C. The needle catch 212 may include elastomeric materials that can be penetrated by the needle 210. The elastomeric materials allow the needle catch 212 to receive and retain the needle 210 until the needle 210 is physically or forceably removed by the operator of the medical device 200.

The needle catch 212 may also be rotated such that the needle 210 can have a new point of entry during each procedure.

Figure 5A:
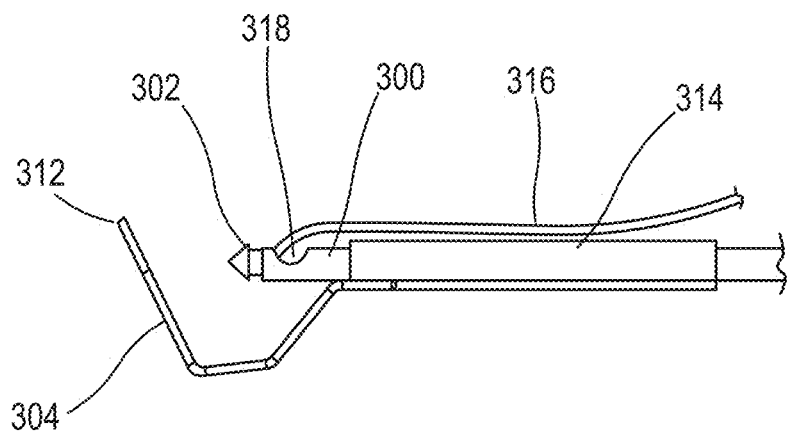
FIG. 5A is a plan view of another embodiment of the needle carrier and needle catch of medical device of FIG. 1A.
Figure 5B:
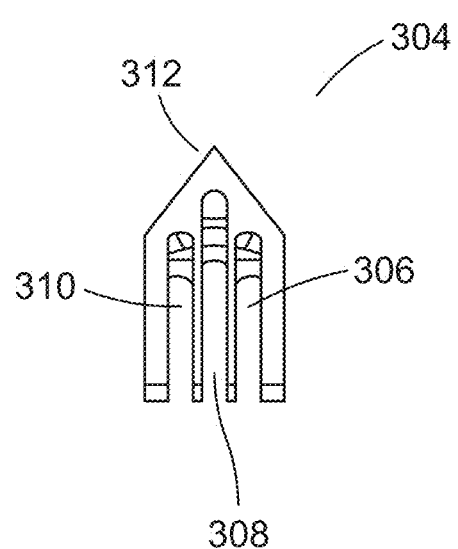
FIG. 5B is a top plan view of the needle catch of FIG. 5A.

Referring to FIGS. 5A and 5B, another embodiment according to the invention is depicted as a needle carrier 300, needle 302, and needle catch 304. In contrast to all other embodiments described with respect to FIGS. 1A-1B and FIGS. 4A-4B, which describe a needle catch disposed proximal to a needle carrier, the needle catch 304 is disposed distal to the needle carrier 300 and the needle 302. The needle catch 304 is provided with a first opening 308, a second opening 310, and third opening 312. The needle catch 304 may be provided in various shapes and sizes in order to accommodate the requirements of the operator, such as a substantially V-shaped configuration. The needle catch 304 further includes a sharpened pointed tip 314. The pointed tip 314 can be used to penetrate tissue. In operation, the needle catch 304 functions as does the needle catch 112 of FIG. 1A. In addition, the needle carrier 300 and the needle catch 304 may be manipulated by a knob member 114 as shown in FIG. 1A. The needle 302 may be coupled to a suture 316 through an inlet 318 disposed on the distal end of the needle carrier 300.

In various embodiments, other means may be used to construct the medical device 100, including, but not limited to, glue, welding, sonic welding, insert molding, or use of fasteners. The elongated shaft member 104 can be of a shape other than tubular or cylindrical, such as elliptical or rectangular. The shape and material chosen for the medical device 100 will vary to suit a particular application.

In one embodiment according to the invention, the medical device 100 of FIG. 1A may have the following dimensions. These dimensions are merely exemplary and other dimensions may be contemplated. For example, the length of the elongated shaft member 104 from the distal end of the handle 102 to the needle carrier 108 is about 3.5 inches. This length may be greater or lesser than 3.5 inches in other embodiments. In addition, a diameter of the elongated shaft member 104 is about 1.25 inches.

It will be understood that various modifications may be made to the embodiments disclosed herein. Therefore, the above description should not be construed as limiting, but merely as illustrative of some embodiments according to the invention.

What is claimed is:

1. A medical device comprising:
    a handle;
    an elongated shaft member extending from the handle;
    a needle carrier extending from a distal end of the elongated shaft member, the needle carrier including a channel configured to receive a needle that can be coupled to a suture or a portion of a pelvic floor repair implant;
    a slideable mechanism comprising a knob member and an outer shaft, the outer shaft extending from the knob member, the knob member and the outer shaft being disposed coaxially over the elongated shaft member and being manipulatable by an operator of the device to slide along at least a portion of the length of the elongated shaft member; and
    a needle catch configured to receive and retain the needle carried by the needle carrier,
    wherein the slideable mechanism is configured to move the needle carrier along at least the portion of the length of the elongated shaft member while the needle catch remains stationary when the knob member is manipulated by the operator of the device.

2. The medical device of claim 1 wherein the needle catch includes a first opening and a second opening, the needle catch being configured to receive the needle through the first opening and to retain the needle after the needle carrier is retracted, the needle catch being configured to release the needle through the second opening.

3. The medical device of claim 1 wherein the needle carrier has a substantially C-shaped configuration.

4. The medical device of claim 1 wherein the distal portion of the elongated shaft member is deflectable off of the longitudinal axis by manipulation by the operator of the device.

5. The medical device of claim 1 wherein the needle catch is comprised of elastomeric materials and is integrally formed with the outer shaft.

6. The medical device of claim 1 wherein the distance between the needle catch and the needle carrier defines an opening for receiving tissue of a patient's body.

7. The medical device of claim 6, wherein the needle catch includes a sharpened tip for penetrating the tissue of the patient's body.

8. The medical device of claim 1 wherein the proximal portion of the elongated shaft member includes at least one detent.

9. The medical device of claim 8 wherein the at least one detent is configured to prevent movement of the knob member beyond the at least one detent.

10. A medical device comprising:
    a handle;
    an elongated shaft member extending from the handle, the elongated shaft member having a longitudinal axis, the elongated shaft member including a distal portion deflected off the longitudinal axis of the elongated shaft member;
    a needle carrier extending from a distal end of the distal portion of the elongated shaft member, the needle carrier including a channel configured to receive a needle that can be coupled to a suture or a portion of a pelvic floor repair implant;
    a slideable mechanism comprising a knob member and an outer shaft, the outer shaft extending from the knob member, the knob member and a first portion of the outer shaft being configured to coaxially move over the elongated shaft member along the longitudinal axis, a second portion of the outer shaft being configured to move along the longitudinal axis such that the second portion of the outer shaft does not move coaxially over the elongated shaft member; and
    a needle catch configured to receive and retain the needle carried by the needle carrier, the needle catch coupled to a distal end of the second portion of the outer shaft,
    wherein the slideable mechanism is configured to move the needle catch relative to the needle carrier along the longitudinal axis when the knob member is manipulated by the operator of the device.

11. The medical device of claim 10 wherein the needle catch includes a first opening and a second opening, the needle catch being configured to receive the needle through the first opening and to retain the needle after the needle carrier is retracted, the needle catch being configured to release the needle through the second opening.

12. The medical device of claim 10 wherein the distal portion of the elongated shaft member is deflectable off of the longitudinal axis by manipulation by the operator of the device.

13. The medical device of claim 10 wherein the needle catch is comprised of elastomeric materials and is integrally formed with the outer shaft.

14. The medical device of claim 10 wherein the distance between the needle catch and the needle carrier defines an opening for receiving tissue of a patient's body.

15. The medical device of claim 10 wherein the proximal portion of the elongated shaft member includes at least one detent.

16. The medical device of claim 15 wherein the at least one detent is configured to prevent movement of the knob member beyond the at least one detent.

17. A method of delivering a suture or an implant, the method comprising:

proving a medical device, the medical device including a handle, an elongated shaft member extending from the handle, a needle carrier extending from a distal end of the elongated shaft member, a slideable mechanism including a knob member and an outer shaft extending from the knob member, and a needle catch coupled to a distal end portion of the outer shaft, the needle carrier including a channel configured to receive a needle that can be coupled to a suture or a portion of a pelvic floor repair implant, the knob member and the outer shaft being partially disposed coaxially over the elongated shaft member such that a proximal end portion of the outer shaft moves coaxially over the elongated shaft member and the distal end portion of the outer shaft does not move coaxially over the elongated shaft member, the needle catch configured to receive and retain the needle carried by the needle carrier;

inserting the needle coupled to the suture or the portion of the pelvic floor repair implant into the needle carrier;

dissecting a patient's body to create an opening within the patient's body;

inserting the elongated shaft member and the needle carrier through the opening;

manipulating the needle carrier around a tissue portion within the opening; and manipulating the slideable mechanism to move the needle catch relative to the needle carrier to cause the needle to be pushed through the tissue portion into the needle catch.

* * * * *